United States Patent
Balaji et al.

(10) Patent No.: US 10,660,576 B2
(45) Date of Patent: May 26, 2020

(54) SYSTEM AND METHOD FOR DETECTING RETINOPATHY

(71) Applicant: Cognizant Technology Solutions India Pvt. Ltd., Chennai (IN)

(72) Inventors: Mahesh Balaji, Chennai (IN); Venugopal Gundimeda, Hyderabad (IN); Parthasarathi Jinka, Tirupati (IN); Rajkumar Joseph, Chennai (IN); Sakthi Indra Sambandam, Chennai (IN); Ratan Sundarrajan Murali, Chennai (IN); Vinayaka Raj, Kanyakumari District (IN)

(73) Assignee: COGNIZANT TECHNOLOGY SOLUTIONS INDIA PVT. LTD., Chennai (IN)

( * ) Notice: Subject to any disclaimer, the term of this patent is extended or adjusted under 35 U.S.C. 154(b) by 336 days.

(21) Appl. No.: 15/690,662

(22) Filed: Aug. 30, 2017

(65) Prior Publication Data

US 2018/0214087 A1  Aug. 2, 2018

(30) Foreign Application Priority Data

Jan. 30, 2017 (IN) .............................. 201741003340

(51) Int. Cl.
*A61B 5/00* (2006.01)
*G06T 7/00* (2017.01)
(Continued)

(52) U.S. Cl.
CPC .......... *A61B 5/7264* (2013.01); *A61B 3/0025* (2013.01); *A61B 3/12* (2013.01);
(Continued)

(58) Field of Classification Search
CPC . G06T 2207/30041; G06T 2207/20081; G06T 2207/20084; A61B 3/0025;
(Continued)

(56) References Cited

U.S. PATENT DOCUMENTS

| 2016/0063359 A1 | 3/2016 | Szegedy et al. |
| 2016/0117587 A1 | 4/2016 | Yan |

(Continued)

OTHER PUBLICATIONS

"Convolutional Neural Networks for Diabetic Retinopathy" by H. Pratt et al., Procedia Computer Science. 90. pp. 200-205 (Jul. 2016) (Year: 2016).*

(Continued)

*Primary Examiner* — Jeffrey G Hoekstra
*Assistant Examiner* — Jason M Ip
(74) *Attorney, Agent, or Firm* — Cantor Colburn LLP (57) ABSTRACT

A system and computer-implemented method for detecting retinopathy is provided. The system comprises an image input module configured to receive one or more fundus images. Further, the system comprises a pre-processing module configured to apply one or more transformations to the one or more received fundus images. Furthermore, the system comprises a feature extraction module configured to extract one or more features from the one or more transformed images using one or more Convolutional Neural Networks (CNNs). Also, the system comprises a prediction module configured to determine stage of retinopathy by classifying the one or more extracted features using pre-stored features, wherein the pre-stored features are extracted from one or more training fundus images by the one or more CNNs and further wherein each pre-stored feature corresponds to a class which is associated with a predetermined stage of retinopathy.

18 Claims, 4 Drawing Sheets

(51) Int. Cl.
*G06K 9/46* (2006.01)
*A61B 3/12* (2006.01)
*G06K 9/62* (2006.01)
*A61B 3/00* (2006.01)
*G06K 9/00* (2006.01)

(52) U.S. Cl.
CPC .......... *A61B 5/7253* (2013.01); *G06K 9/0061* (2013.01); *G06K 9/4604* (2013.01); *G06K 9/4628* (2013.01); *G06K 9/6269* (2013.01); *G06K 9/6274* (2013.01); *G06T 7/0012* (2013.01); *G06K 9/628* (2013.01); *G06K 9/6277* (2013.01); *G06K 2209/051* (2013.01); *G06T 2207/20081* (2013.01); *G06T 2207/20084* (2013.01); *G06T 2207/30041* (2013.01)

(58) Field of Classification Search
CPC .... A61B 3/12; A61B 5/7267; G06K 2209/05; G06K 9/0061; G06K 9/00617; G06K 9/4628; G06K 9/00597; G06K 9/36; G06K 9/46; G06K 9/4623; G06N 3/0454
See application file for complete search history.

(56) References Cited

U.S. PATENT DOCUMENTS

2016/0292856 A1    10/2016  Niemeijer
2019/0191988 A1*   6/2019   Gargeya ................ A61B 3/12

OTHER PUBLICATIONS

"Automated Identification of Diabetic Retinopathy Stages Using Digital Fundus Images" by J. Nayak et al. J Med. Syst. (2008) 32: 107-115 (Year: 2008).*

"Diabetic Retinopathy Detection Through Image Analysis Using Deep Convolutional Neural Networks" by J. De La Torre et al. Artificial Intelligence Research and Development. 2016. pp. 58-63 (Year: 2016).*

Avisek Lahiri, Abhijit Guha Roy, Debdoot Sheet, Prabir Kumar Biswas; Deep neural ensemble for retinal vessel segmentation in fundus images towards achieving label-free angiography; 2016 38th Annual International Conference of the IEEE Engineering in Medicine and Biology Society (EMBC); Aug. 16-20, 2016; Orlando, FL, USA; http://ieeexplore.ieee.org/document/7590955/.

Chandrakumar T, R Kathirvel; Classifying Diabetic Retinopathy using Deep Learning Architecture; International Journal of Engineering Research & Technology; vol. 5—Issue. 06 , Jun. 2016; https://www.ijert.org/view-pdf/15351/classifying-diabetic-retinopathy-using-deep-learning-architecture.

Dan Ciresan, Ueli Meier, Jurgen Schmidhuber; Multi-column Deep Neural Networks for Image Classification; CVPR 2012, p. 3642-3649; http://people.idsia.ch/~ciresan/data/cvpr2012.pdf.

Debapriya Maji, Anirban Santara, Pabitra Mitra, Debdoot Sheet; Ensemble of Deep Convolutional Neural Networks for Learning to Detect Retinal Vessels in Fundus Images; ArXiv; 2016; https://arxiv.org/pdf/1603.04833.pdf.

Gilbert Lim, Mong Li Lee, Wynne Hsu, Tien Yin Wong; Transformed Representations for Convolutional Neural Networks in Diabetic Retinopathy Screening; AAAI Publications, Workshops at the Twenty-Eighth AAAI Conference on Artificial Intelligence; 2014; https://www.aaai.org/ocs/index.php/WS/AAAIW14/paper/viewFile/8754/8305.

* cited by examiner

SYSTEM AND METHOD FOR DETECTING RETINOPATHY

CROSS REFERENCE TO RELATED APPLICATION

This application is related to and claims the benefit of Indian Patent Application No. 201741003340 filed on Jan. 30, 2017, the contents of which are herein incorporated by reference in their entirety.

FIELD OF THE INVENTION

The present invention relates generally to detecting retinopathy. More particularly, the present invention provides a system and method for automatically and accurately detecting retinopathy.

BACKGROUND OF THE INVENTION

Diabetic retinopathy is an eye disease which is associated with long-standing diabetes. Vision impairment may be prevented using laser treatments if diabetic retinopathy is detected early. However, early detection of diabetic retinopathy is challenging as diabetic retinopathy does not show explicit symptoms until it reaches advance stages.

Conventionally, diabetic retinopathy is detected manually by physicians and ophthalmologists. However, manual detection of diabetic retinopathy has many disadvantages such as lack of experience. Also, manually detecting diabetic retinopathy is a time-consuming process. Further, delay in screening process leads to delayed or no follow-up, miscommunication and delayed treatment thereby increasing the probability of vision loss.

To overcome the disadvantages of manual detection, systems and methods exist that facilitate automatic detection of retinopathy. For instance, systems exist that use training data to build datasets and algorithms for detecting retinopathy from digital fundus images. However, the above-mentioned systems also suffer from various disadvantages. The abovementioned systems are incapable of processing noisy images, out of focus images, underexposed and overexposed images. Also, these systems are not able to predict retinopathy with certainty thereby facilitating need of a confirmatory screening by specialists.

In light of the abovementioned disadvantages, there is a need for a system and method for automated detection of retinopathy, particularly diabetic retinopathy. Further, there is a need for a system and method which is capable of efficiently processing images captured from color fundus camera for detecting retinopathy. Furthermore, there is a need for a system and method capable of accurately detecting retinopathy and if required, promptly referring the patients to specialists. In addition, there is a need for a learning based system and method that uses pattern recognition with feedback loop. Also, there is a need for a system and method that is scalable, cost-effective, capable of processing multiple images, lowers dependency on human intervention and facilitates in providing more time to medical practitioners.

SUMMARY OF THE INVENTION

A system, computer-implemented method and computer program product for detecting retinopathy is provided. The system comprises an image input module configured to receive one or more fundus images. Further, the system comprises a pre-processing module configured to apply one or more transformations to the one or more received fundus images. Furthermore, the system comprises a feature extraction module configured to extract one or more features from the one or more transformed images using one or more Convolutional Neural Networks (CNNs). Also, the system comprises a prediction module configured to determine stage of retinopathy by classifying the one or more extracted features using pre-stored features, wherein the pre-stored features are extracted from one or more training fundus images by the one or more CNNs and further wherein each pre-stored feature corresponds to a class which is associated with a predetermined stage of retinopathy.

In an embodiment of the present invention, the one or more transformations comprise at least one of: contrast stretching and hue transformation. In an embodiment of the present invention, the one or more features are extracted from the one or more transformed images by passing the one or more transformed images through one or more layers of the CNNs thereby extracting details corresponding to one or more points of interest within the one or more transformed images.

In an embodiment of the present invention, the one or more extracted features are classified by matching each of the one or more extracted features with the pre-stored features and further wherein the stage of retinopathy is determined based on the predetermined stage of retinopathy associated with the class corresponding to each of the matched pre-stored features.

In an embodiment of the present invention, the one or more fundus images are of one or more patients. In an embodiment of the present invention, each training fundus image represents a specific predetermined stage of retinopathy and is classified based on the specific predetermined stage of retinopathy and further wherein the pre-stored features extracted from the training fundus image corresponds to the class associated with the training fundus image. In an embodiment of the present invention, the predetermined stage of retinopathy is one of: absence of retinopathy, mild retinopathy, moderate retinopathy, severe retinopathy and proliferative retinopathy.

The computer-implemented method for detecting retinopathy, via program instructions stored in a memory and executed by a processor, comprises receiving one or more fundus images. The computer-implemented method further comprises applying one or more transformations to the one or more received fundus images. Furthermore, the computer-implemented method comprises extracting one or more features from the one or more transformed images using one or more Convolutional Neural Networks (CNNs). In addition, the computer-implemented method comprises determining stage of retinopathy by classifying the one or more extracted features using pre-stored features, wherein the pre-stored features are extracted from one or more training fundus images by the one or more CNNs and further wherein each pre-stored feature corresponds to a class which is associated with a predetermined stage of retinopathy.

The computer program product for detecting retinopathy comprises a non-transitory computer-readable medium having computer-readable program code stored thereon, the computer-readable program code comprising instructions that when executed by a processor, cause the processor to receive one or more fundus images. The processor further applies one or more transformations to the one or more received fundus images. Furthermore, the processor extracts one or more features from the one or more transformed images using one or more Convolutional Neural Networks (CNNs). The processor also determines stage of retinopathy by classifying the one or more extracted features using pre-stored features, wherein the pre-stored features are extracted from one or more training fundus images by the one or more CNNs and further wherein each pre-stored feature corresponds to a class which is associated with a predetermined stage of retinopathy.

BRIEF DESCRIPTION OF THE ACCOMPANYING DRAWINGS

The present invention is described by way of embodiments illustrated in the accompanying drawings wherein.

DETAILED DESCRIPTION OF THE INVENTION

A system and method for automated detection of retinopathy is described herein. The invention provides a system and method which is capable of efficiently processing images of eye captured using color fundus camera for detecting retinopathy. The invention further provides a system and method capable of accurately detecting retinopathy and if required, promptly referring the patients to specialists. In addition, the invention provides a learning based system and method that uses pattern recognition with feedback loop. Also, the invention provides a system and method that is scalable, cost-effective, capable of processing multiple images, lowers dependency on human intervention and facilitates in providing more time to medical practitioners.

The following disclosure is provided in order to enable a person having ordinary skill in the art to practice the invention. Exemplary embodiments are provided only for illustrative purposes and various modifications will be readily apparent to persons skilled in the art. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

The present invention would now be discussed in context of embodiments as illustrated in the accompanying drawings.

Figure 1:
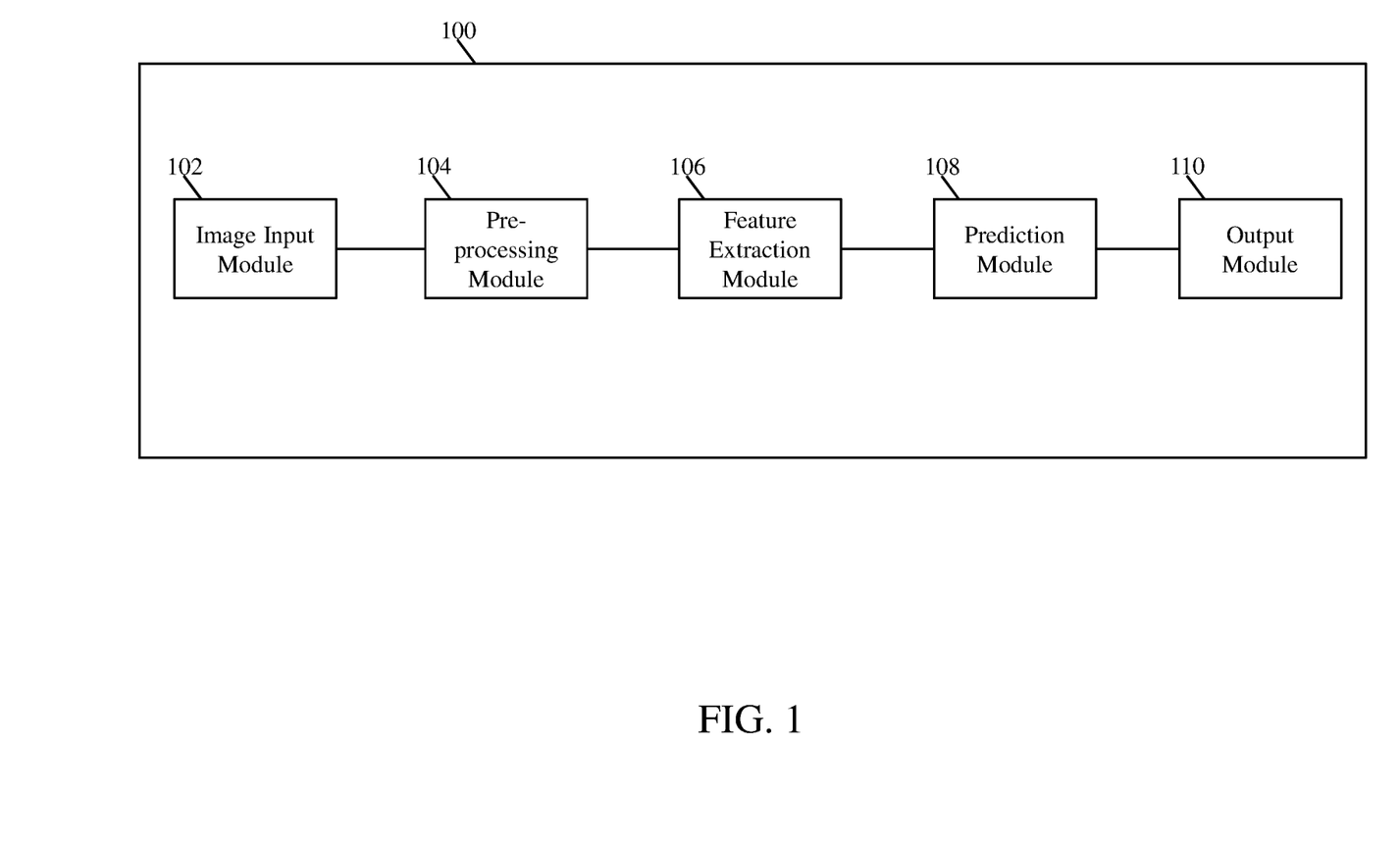
FIG. 1 is a block diagram illustrating a system for automatically detecting retinopathy, in accordance with an embodiment of the present invention.

FIG. 1 is a block diagram illustrating a system 100 for automatically detecting retinopathy, in accordance with an embodiment of the present invention. The system 100 comprises an image input module 102, a pre-processing module 104, a feature extraction module 106, a prediction module 108 and an output module 110.

The system 100 is initially trained using one or more training fundus images. During training, the one or more training fundus images are received and classified by the image input module 102. In an embodiment of the present invention, the one or more training fundus images are high resolution images of the fundus taken using different cameras under various imaging conditions. Further, each of the one or more received training fundus images represent a specific predetermined stage of retinopathy and are classified based on the specific predetermined stage of retinopathy. In an exemplary embodiment of the present invention, the training fundus images are classified using numbers 0-4, wherein images of the eye fundus that have no retinopathy (absence of retinopathy) belong to class 0, images of the eye fundus that have mild retinopathy belong to class 1, images of the eye fundus that have moderate retinopathy belong to class 2, images of the eye fundus that have severe retinopathy belong to class 3 and images of the eye fundus that have proliferative retinopathy and belong to class 4.

After classification, the one or more classified images are forwarded to the pre-processing module 104 by the image input module 102. The pre-processing module 104 is configured to apply one or more transformations to the one or more classified images. In an embodiment of the present invention, the one or more transformations include, but not limited to, contrast stretching and hue transformation. Contrast stretching is an image enhancement technique which improves the contrast of an image by stretching the range of intensity values to span a desired range of values. Another transformation is hue. The RGB color space has no intrinsic relation to the natural color properties and neither to human interpretation of color, however hue represents how humans perceive color. Hue is one of the main properties (called color appearance parameters) of a color. Applying the hue transformation makes the algorithm less sensitive if not invariant to lighting variations.

After applying the one or more transformations, the pre-processing module 104 creates two versions of each of the one or more classified images. All the images are then normalized to represent each class equally in the training process.

The feature extraction module 106 comprises of one or more Convolutional Neural Networks (CNNs) configured to extract features from the one or more normalized images received from the pre-processing module 104. The architecture of a CNN is designed to take advantage of the structure of an input image. This is achieved with local receptive fields and shared weights followed by pooling which results in translation invariant features. Another advantage of using CNNs is self-feature extraction. CNN based Feature exaction facilitates in capturing low, mid and high level image features automatically.

During feature extraction, details from one or more points of interest within the one or more normalized images are extracted intelligently and stored as features. Further, each stored feature from the one or more normalized images corresponds to the class associated with the normalized image from which it was extracted.

In an exemplary embodiment of the present invention, the feature extraction module 106 comprises of five CNNs. Further, by using five CNNs, the feature extraction module 106 facilitates each CNN to extract features specific to a class representing a specific stage of retinopathy and avoiding loss of information. Furthermore, each CNN is designed to concentrate on a particular stage of the disease and learn morphological differences between images of each stage of retinopathy thereby improving performance by using features extracted from five CNNs instead of only one CNN.

Each CNN is inputted with a set of images belonging to a particular class and representing a specific stage of retinopathy. For instance, the first CNN is inputted with normalized images of the fundus having no retinopathy that belong to class 0, the second CNN is inputted with normalized images of the fundus having mild retinopathy that belong to class 1 and so on. Further, classifying the one or more training fundus images facilitates in extracting features and class probabilities of the extracted features by corresponding CNN thereby facilitating efficient identification of specific stage of the disease. The feature extraction module is discussed in detail in conjunction with FIG. 2.

Figure 2:
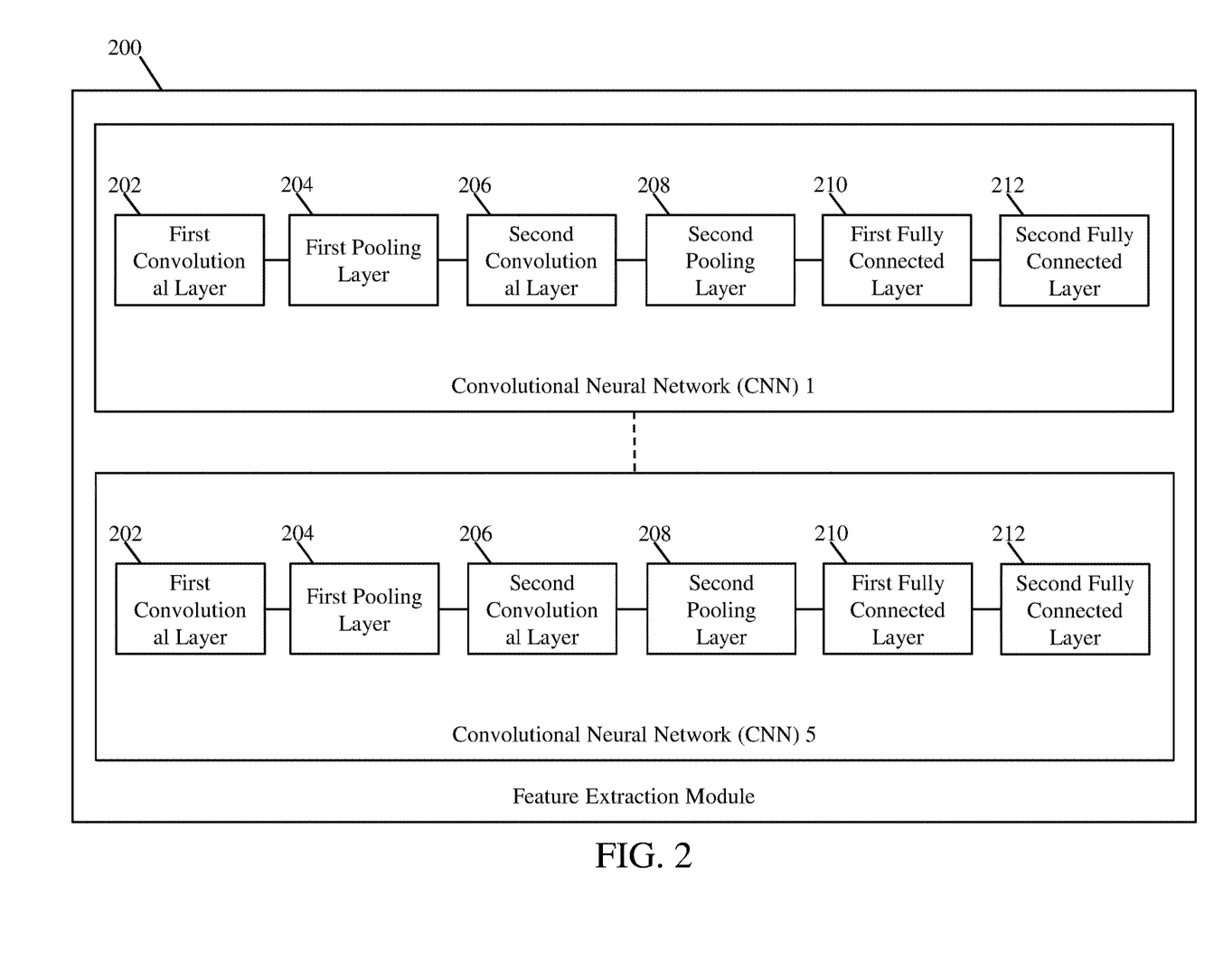
FIG. 2 is a detailed block diagram illustrating a feature extraction module, in accordance with an exemplary embodiment of the present invention.

FIG. 2 is a detailed block diagram illustrating a feature extraction module 200, in accordance with an embodiment of the present invention.

In an embodiment of the present invention, the feature extraction module 200 comprises of five CNNs. Further, each CNN comprises a first convolutional layer 202, a first pooling layer 204, a second convolutional layer 206, a second pooling layer 208, a first fully connected layer 210 and a second fully connected layer 212.

The first convolutional layer 202 consist of a rectangular grid of neurons configured to apply weights in the form of potential filters on the one or more normalized images received from the pre-processing module 104 (FIG. 1). After the one or more normalized images pass through the first convolutional layer 202, the first pooling layer 204 subsamples output of the first convolutional layer 202 to produce a single output. In an embodiment of the present invention, the first pooling layer 204 uses maximum pooling to take maximum block for pooling. The output of the first pooling layer 204 is then provided as input to the second convolutional layer 206. The second convolutional layer 206 also consists of a rectangular grid of neurons which applies weights in the form of potential filters to the input received from the first pooling layer 204 and forwards the output to the second pooling layer 208. The second pooling layer 208, similar to the first pooling layer 204, subsamples the output of the second convolutional layer 206. After pooling, the control is transferred to the first fully connected layer 210.

The first fully connected layer 210 connects each of its neurons with each neuron of the second pooling layer 208. Further, the first fully connected layer 210 provides a one-dimensional representation of features extracted from the one or more normalized images. The output of the first fully connected layer 210 acts as an input to the second fully connected layer 212. Further, the second fully connected layer 212 also provides one-dimensional representation of features extracted from the one or more normalized images. Furthermore, using two fully connected layers facilitate in reducing under-fitting of the neural network, providing non-linear functionality, increasing feature learnability, increasing generalization, increasing accuracy and feature hierarchy to learn distinct set of features in each layer. In an embodiment of the present invention, the CNNs further comprise a softmax function module which is used for multiclass classification. The softmax function facilitates in categorical distribution that is a probability distribution over various different possible outcomes.

In an exemplary embodiment of the present invention, the first CNN is a multiclass classification model with classes as 0 vs 1 vs 2 vs 3 vs 4. The first CNN extracts 150 features and 5 class probabilities from each image. Further, since two versions of each image are processed thereby total of 310 features are extracted. The second is a binary classification model with classes 0 vs 1 vs 2, 3 and 4. The second CNN extracts 150 features and 3 class probabilities from each image thereby a total of 306 features for two versions of each image. The third CNN is also a binary classification model with classes 0, 1 vs 2, 3, and 4. The third CNN extracts 150 features and 2 class probabilities from each image thereby a total of 304 features for two versions of each image. The fourth CNN is also a binary classification model with classes 0, 1, 2 vs 3, 4. The fourth CNN extracts 150 features and 2 class probabilities from each image thereby a total of 304 features for two versions of each image. The fifth CNN is also a binary classification model with classes 0 vs 1, 2 vs 3, 4. The fifth CNN extracts 150 features and 3 class probabilities from each image thereby a total of 306 features for two versions of each image. The features and the class probabilities extracted by the five CNNs are stored in the prediction module (FIG. 1) and are used during detection process.

In an embodiment of the present invention, the prediction module 108 is also trained using the features and class probabilities extracted during the training process. After training, the prediction module 108 is considered trained for detecting the stage of the disease in the form of class probabilities.

Referring back to FIG. 1, the system 100 is considered to be trained after extraction of features from the one or more training fundus images. Further, the trained system 100 is capable of detecting retinopathy using one or more fundus images of one or more patients.

During the detection process, the image input module 102 is configured to receive and forward the one or more fundus images of the one or more patients to the pre-processing module 104. The pre-processing module 104 is configured to apply one or more transformations to the one or more received fundus images. After applying the transformations, the one or more transformed images are forwarded to the CNNs within the feature extraction module 106 for feature extraction. Further, one or more features are extracted from the one or more transformed images by passing the one or more transformed images through one or more layers of the CNNs thereby extracting details corresponding to one or more points of interest (referred to as features) within the one or more transformed images. The features extracted by the CNNs are then forwarded to the prediction module 108.

The prediction module 108 comprises a classifier that uses pre-stored features and their corresponding class probabilities extracted by the CNNs during training process to predict the stage of the disease. The prediction module 108 passes the features, extracted during the detection process, through the classifier to determine stage of retinopathy by classifying the one or more extracted features using pre-stored features. Further, the one or more extracted features are classified by matching each of the one or more extracted features with the pre-stored features. Once an extracted feature matches with a pre-stored feature, the class corresponding to the matched pre-stored feature is associated with the corresponding extracted feature. The prediction module 108 then determines stage of retinopathy of the one or more patients based on the predetermined stage of retinopathy associated with the class corresponding to each of the matched pre-stored features. In an embodiment of the present invention, the prediction module 108 considers the class corresponding to each of the one or more matched pre-stored features to determine the stage of retinopathy. In an embodiment of the present invention, the prediction module 108 determines the stage of retinopathy for a fundus image of a patient as the predetermined stage of retinopathy associated with the class corresponding to maximum matched pre-stored features of the fundus image.

In an embodiment of the present invention, the prediction module 108 contains a classification model which ensures bias-variance trade-off by employing regularization and boosting. Further, regularization facilitates in reduces over-fitting model (variance) and boosting facilitates in reducing under-fitting (Bias). Further, the prediction module 108 applies greater than condition to identify presence or absence of retinopathy in the one or more fundus images provided for the detection process.

The output module 110 is configured to provide the results of the detection process to one or more users of the system 100. In an embodiment of the present invention, the one or more users of the system 100 comprise, the one or more patients, one or more ophthalmologists, one or more physicians and any other stakeholder/concerned person. In an embodiment of the present invention, the output module 110 is configured to provide the results of the detection process in various formats. In an exemplary embodiment of the present invention, the results are provided in the form of a report in Portable Document Format (PDF). In an embodiment of the present invention, the results are provided to the one or more users automatically via one or more communication channels in real-time. Further, the one or more communication channels include, but not limited to, electronic mail, Short Messaging Service (SMS) and instant messaging services.

In an embodiment of the present invention, the system 100 is capable of processing multiple images at a time. In an exemplary embodiment of the present invention, the system 100 processes twenty images at a time. In an embodiment of the present invention, the system 100 uses pattern recognition with feedback loop. In an embodiment of the present invention, the system 100 is a cloud based server. Further, the system 100 comprises an enabled Graphics Processing Unit (GPU) accelerator. Furthermore, image processing libraries are installed and used by the pre-processing module 104 to transform the labeled images before training. Also, the feature extraction module 106 uses a deep learning framework to train feature extraction model with transformed images and saves the feature extraction model for later use.

Figure 3:
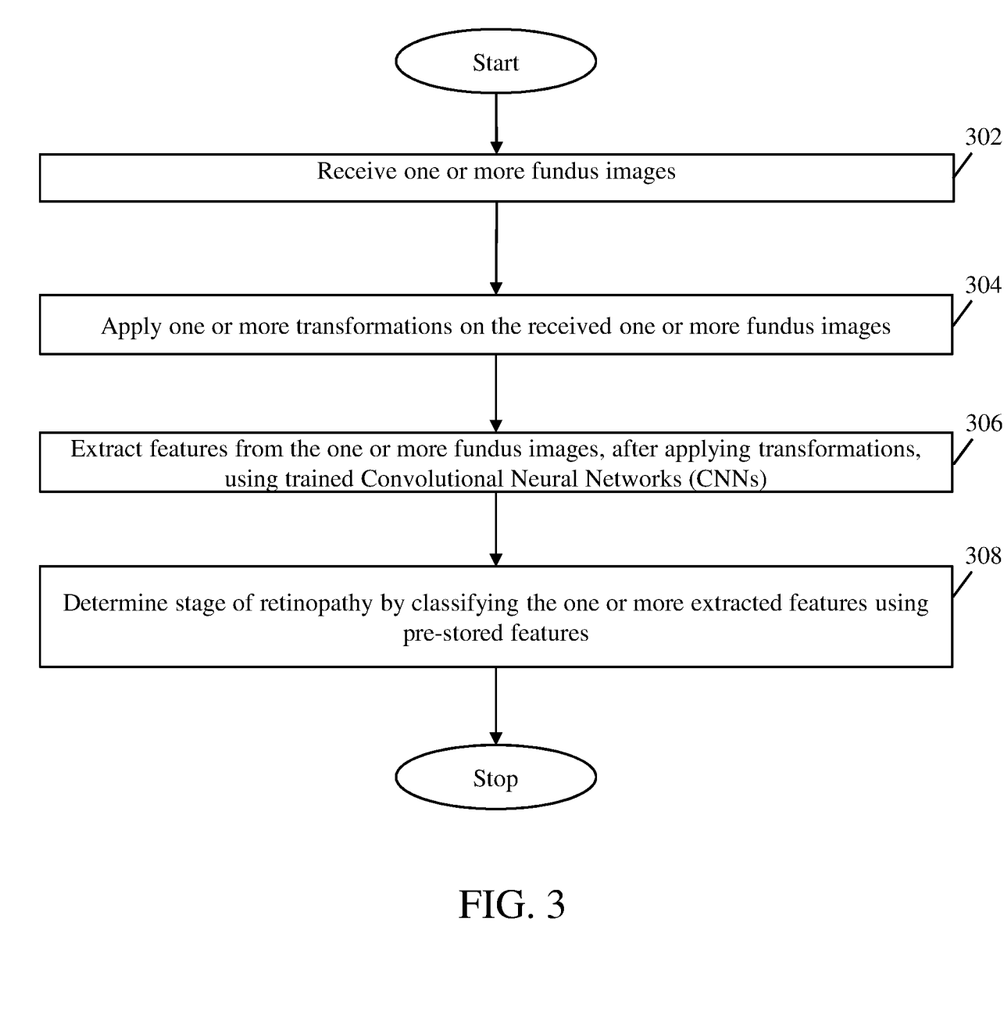
FIG. 3 is a flowchart illustrating a system for automatically detecting retinopathy, in accordance with an embodiment of the present invention.

FIG. 3 is a flowchart illustrating a system for automatically detecting retinopathy, in accordance with an embodiment of the present invention.

At step 302, one or more fundus images of one or more patients are received for determining presence or absence of retinopathy. At step 304, one or more transformations are applied to the one or more received fundus images. In an embodiment of the present invention, the one or more transformations comprise at least one of: contrast stretching and hue transformation.

At step 306, one or more features from the one or more transformed images are extracted using one or more Convolutional Neural Networks (CNNs). In an embodiment of the present invention, the one or more features are extracted from the one or more transformed images by passing the one or more transformed images through one or more layers of the CNNs thereby extracting details corresponding to one or more points of interest within the one or more transformed images. In an exemplary embodiment of the present invention, five CNNs are employed for feature extraction. In an exemplary embodiment of the present invention, each CNN comprises two convolutional layers, two pooling layers and two fully connected layers.

At step 308, stage of retinopathy is determined by classifying the one or more extracted features using pre-stored features. In an embodiment of the present invention, the pre-stored features are extracted from one or more training fundus images during a training process by the one or more CNNs. Further, each pre-stored feature corresponds to a class which is associated with a predetermined stage of retinopathy. In an exemplary embodiment, the predetermined stage of retinopathy is one of: absence of retinopathy, mild retinopathy, moderate retinopathy, severe retinopathy and proliferative retinopathy.

In an embodiment of the present invention, during the training process, each training fundus image represents a specific predetermined stage of retinopathy and is classified based on the specific predetermined stage of retinopathy. Further, the pre-stored features extracted from the training fundus image corresponds to the class associated with the training fundus image.

For determining the stage of retinopathy, the one or more extracted features are classified by matching each of the one or more extracted features with the pre-stored features. Further, the stage of retinopathy is determined based on the predetermined stage of retinopathy associated with the class corresponding to each of the matched pre-stored features. In an embodiment of the present invention, stage of retinopathy for a fundus image of a patient is determined as the predetermined stage of retinopathy associated with the class corresponding to maximum matched pre-stored features of the fundus image.

Figure 4:
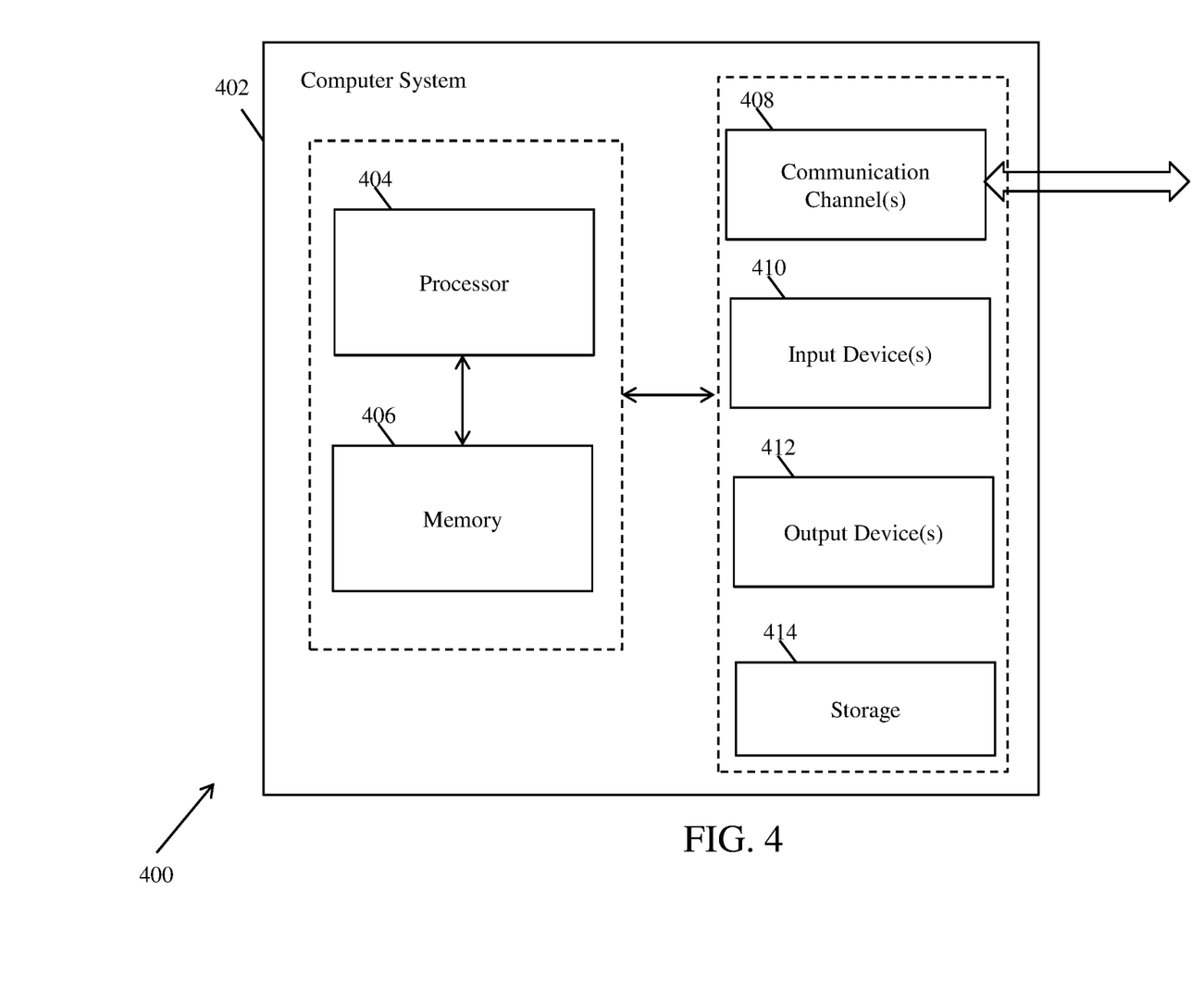
FIG. 4 illustrates an exemplary computer system for automatically detecting retinopathy, in accordance with an embodiment of the present invention.

FIG. 4 illustrates an exemplary computer system for automatically detecting retinopathy, in accordance with an embodiment of the present invention.

The computer system 402 comprises a processor 404 and a memory 406. The processor 404 executes program instructions and may be a real processor. The processor 404 may also be a virtual processor. The computer system 402 is not intended to suggest any limitation as to scope of use or functionality of described embodiments. For example, the computer system 402 may include, but not limited to, a general-purpose computer, a programmed microprocessor, a micro-controller, a peripheral integrated circuit element, and other devices or arrangements of devices that are capable of implementing the steps that constitute the method of the present invention. In an embodiment of the present invention, the memory 406 may store software for implementing various embodiments of the present invention. The computer system 402 may have additional components. For example, the computer system 402 includes one or more communication channels 408, one or more input devices 410, one or more output devices 412, and storage 414. An interconnection mechanism (not shown) such as a bus, controller, or network, interconnects the components of the computer system 402. In various embodiments of the present invention, operating system software (not shown) provides an operating environment for various softwares executing in the computer system 402, and manages different functionalities of the components of the computer system 402.

The communication channel(s) 408 allow communication over a communication medium to various other computing entities. The communication medium provides information such as program instructions, or other data in a communication media. The communication media includes, but not limited to, wired or wireless methodologies implemented with an electrical, optical, RF, infrared, acoustic, microwave, bluetooth or other transmission media.

The input device(s) 410 may include, but not limited to, a keyboard, mouse, pen, joystick, trackball, a voice device, a scanning device, or any another device that is capable of providing input to the computer system 402. In an embodiment of the present invention, the input device(s) 410 may be a sound card or similar device that accepts audio input in analog or digital form. The output device(s) 412 may include, but not limited to, a user interface on CRT or LCD, printer, speaker, CD/DVD writer, or any other device that provides output from the computer system 402.

The storage 414 may include, but not limited to, magnetic disks, magnetic tapes, CD-ROMs, CD-RWs, DVDs, flash drives or any other medium which can be used to store information and can be accessed by the computer system 402. In various embodiments of the present invention, the storage 414 contains program instructions for implementing the described embodiments.

The present invention may suitably be embodied as a computer program product for use with the computer system 402. The method described herein is typically implemented as a computer program product, comprising a set of program instructions which is executed by the computer system 402 or any other similar device. The set of program instructions may be a series of computer readable codes stored on a tangible medium, such as a computer readable storage medium (storage 414), for example, diskette, CD-ROM, ROM, flash drives or hard disk, or transmittable to the computer system 402, via a modem or other interface device, over either a tangible medium, including but not limited to optical or analogue communications channel(s) 408. The implementation of the invention as a computer program product may be in an intangible form using wireless techniques, including but not limited to microwave, infrared, bluetooth or other transmission techniques. These instructions can be preloaded into a system or recorded on a storage medium such as a CD-ROM, or made available for downloading over a network such as the internet or a mobile telephone network. The series of computer readable instructions may embody all or part of the functionality previously described herein.

The present invention may be implemented in numerous ways including as an apparatus, method, or a computer program product such as a computer readable storage medium or a computer network wherein programming instructions are communicated from a remote location.

While the exemplary embodiments of the present invention are described and illustrated herein, it will be appreciated that they are merely illustrative. It will be understood by those skilled in the art that various modifications in form and detail may be made therein without departing from or offending the spirit and scope of the invention as defined by the appended claims.

We claim:

1. A system for classifying fundus image features for detecting retinopathy, the system comprising:
   a memory storing program instructions;
   a processor configured to execute program instructions stored in the memory and configured to;
   classify one or more fundus images based on a predetermined stage of retinopathy;
   apply one or more transformations to the one or more classified fundus images;
   extract a set of features from each of the transformed fundus images using multiple Convolutional Neural Networks (CNNs),wherein each of the multiple CNNs extracts the set of features corresponding to a specific class respectively from the classified transformed fundus images, and wherein the multiple CNNs includes:
   a first CNN including a multiclass classification model extracting a first set of features corresponding to a first set of class probabilities from each of the images;
   a second CNN including a binary classification model extracting a second set of features corresponding to a second set of class probabilities from each of the images;
   a third CNN including a binary classification model extracting a third set of features corresponding to a third set of class probabilities from each of the images;
   a fourth CNN including a binary classification model extracting a fourth set of features corresponding to a fourth set of class probabilities from each of the images; and
   a fifth CNN including a binary classification model extracting a fifth set of features corresponding to a fifth set of class probabilities from each of the images;
   and
   determine a stage of retinopathy by classifying the extracted first, second, third, fourth and fifth set of features based on pre-stored features, wherein the pre-stored features are extracted from one or more training fundus images by the multiple CNNs, and further wherein each pre-stored feature corresponds to a class which is associated with a predetermined stage of retinopathy.

2. The system of claim 1, wherein the one or more transformations comprise at least one of: contrast stretching and hue transformation.

3. The system of claim 1, wherein the one or more features are extracted from the one or more transformed fundus images by passing the one or more transformed fundus images through one or more layers of the multiple CNNs thereby extracting details corresponding to one or more points of interest within the one or more transformed fundus images.

4. The system of claim 1, wherein the one or more extracted features are classified by matching each of the one or more extracted features with the pre-stored features and further wherein the stage of retinopathy is determined based on the predetermined stage of retinopathy associated with the class corresponding to a maximum matched pre-stored features.

5. The system of claim 1 wherein the one or more fundus images are of one or more patients.

6. The system of claim 1, wherein the predetermined stage of retinopathy is one of: absence of retinopathy, mild retinopathy, moderate retinopathy, severe retinopathy and proliferative retinopathy.

7. A computer-implemented method for classifying fundus image features for detecting retinopathy, via program instructions stored in a memory and executed by a processor, the computer-implemented method comprising:
   classifying one or more fundus images based on a predetermined stage of retinopathy;
   applying one or more transformations to the one or more classified fundus images;
   extracting a set of features from each of the transformed fundus images using multiple Convolutional Neural Networks (CNNs), wherein each of the multiple CNNs extracts the features corresponding to a specific class respectively from the classified transformed fundus images, and wherein the multiple CNNs includes;

a first CNN including a multiclass classification model extracting a first set of features corresponding to a first set of class probabilities from each of the images;

a second CNN including a binary classification model extracting a second set of features corresponding to a second set of class probabilities from each of the images;

a third CNN including a binary classification model extracting a third set of features corresponding to a third set of class probabilities from each of the images;

a fourth CNN including a binary classification model extracting a fourth set of features corresponding to a fourth set of class probabilities from each of the images; and a fifth CNN including a binary classification model extracting a fifth set of features corresponding to a fifth set of class probabilities from each of the images; and determining a stage of retinopathy by classifying the extracted first, second, third, fourth and fifth set of features based on pre-stored features, wherein the pre-stored features are extracted from one or more training fundus images by the multiple CNNs, and further wherein each pre-stored feature corresponds to a class which is associated with a predetermined stage of retinopathy.

8. The computer-implemented method of claim 7, wherein the one or more transformations comprise at least one of: contrast stretching and hue transformation.

9. The computer-implemented method of claim 7, wherein the one or more features are extracted from the one or more transformed images by passing the one or more transformed images through one or more layers of the multiple CNNs thereby extracting details corresponding to one or more points of interest within the one or more transformed images.

10. The computer-implemented method of claim 7, wherein the one or more extracted features are classified by matching each of the one or more extracted features with the pre-stored features and further wherein the stage of retinopathy is determined based on the predetermined stage of retinopathy associated with the class corresponding to a maximum matched pre-stored features.

11. The computer-implemented method of claim 7, wherein the predetermined stage of retinopathy is one of: absence of retinopathy, mild retinopathy, moderate retinopathy, severe retinopathy and proliferative retinopathy.

12. A computer program product for classifying fundus image features for detecting retinopathy, the computer program product comprising:

a non-transitory computer-readable medium having computer-readable program code stored thereon, the computer-readable program code comprising instructions that when executed by a processor, cause the processor to:

classify one or more fundus images based on a predetermined stage of retinopathy;

apply one or more transformations to the one or more classified fundus images;

extract a set of features from each of the transformed fundus images using multiple Convolutional Neural Networks (CNNs), wherein each of the multiple CNNs extracts the features corresponding to a specific class respectively from the classified transformed fundus images, and wherein the multiple CNNs includes:

a first CNN including a multiclass classification model extracting a first set of features corresponding to a first set of class probabilities from each of the images;

a second CNN including a binary classification model extracting a second set of features corresponding to a second set of class probabilities from each of the images;

a third CNN including a binary classification model extracting a third set of features corresponding to a third set of class probabilities from each of the images;

a fourth CNN including a binary classification model extracting a fourth set of features corresponding to a fourth set of class probabilities from each of the images; and a fifth CNN including a binary classification model extracting a fifth set of features corresponding to a fifth set of class probabilities from each of the images; and determine a stage of retinopathy by classifying the extracted first, second, third, fourth and fifth set of features based on pre-stored features, wherein the pre-stored features are extracted from one or more training fundus images by the multiple CNNs and further wherein each pre-stored feature corresponds to a class which is associated with a predetermined stage of retinopathy.

13. The system of claim 1, wherein the processor is configured to apply the one or more transformations to at least two versions of the one or more classified fundus images; and extract the one or more features from the at least two versions of each of the transformed fundus images using the multiple Convolutional Neural Networks (CNNs).

14. The system of claim 1, wherein a predetermined number of class probabilities are extracted corresponding to each CNN of the multiple CNNs.

15. The computed-implemented method of claim 7, wherein the step of applying comprises applying the one or more transformations to at least two versions of the one or more classified fundus images; and extracting the one or more features from the at least two versions of each of the transformed fundus images using the multiple Convolutional Neural Networks (CNNs).

16. The computed-implemented method of claim 7, wherein a predetermined number of class probabilities are extracted corresponding to each CNN of the multiple CNNs.

17. The system of claim 1, wherein the second set of features is same in number as the first set of features and the second set of class probabilities is less in number than the first set of class probabilities, the third set of features is same in number as the first set of features and the third set of class probabilities is less in number than the second set of class probabilities, the fourth set of features is same in number as the first set of features and the fourth set of class probabilities is same in number as the third set of class probabilities, and the fifth set of features is same in number as the first set of features and wherein the fifth set of class probabilities is same in number as the second set of class probabilities.

18. The computer-implemented method of claim 7, wherein the second set of features is same in number as the first set of features and the second set of class probabilities is less in number than the first set of class probabilities, the third set of features is same in number as the first set of features and the third set of class probabilities is less in number than the second set of class probabilities, the fourth set of features is same in number as the first set of features and the fourth set of class probabilities is same in number as the third set of class probabilities, and the fifth set of features is same in number as the first set of features and wherein the fifth set of class probabilities is same in number as the second set of class probabilities.

\* \* \* \* \*